US009335249B2

(12) United States Patent
Matlack et al.

(10) Patent No.: US 9,335,249 B2
(45) Date of Patent: May 10, 2016

(54) TAPE ADHESION TEST SYSTEM

(71) Applicant: Schlumberger Technology Corporation, Sugar Land, TX (US)

(72) Inventors: Bradley Matlack, Overland Park, KS (US); Gregory H. Manke, Overland Park, KS (US); William Goertzen, Lawrence, KS (US); Patrick Zhiyuan Ma, Ct. Lawrence, KS (US); Sayak Datta, Lawrence, KS (US); Mark A. Metzger, Lawrence, KS (US)

(73) Assignee: Schlumberger Technology Corporation, Sugar Land, TX (US)

( * ) Notice: Subject to any disclaimer, the term of this patent is extended or adjusted under 35 U.S.C. 154(b) by 358 days.

(21) Appl. No.: 13/925,654

(22) Filed: Jun. 24, 2013

(65) Prior Publication Data

US 2014/0000356 A1    Jan. 2, 2014

Related U.S. Application Data

(60) Provisional application No. 61/665,298, filed on Jun. 27, 2012.

(51) Int. Cl.
| G01N 19/04 | (2006.01) |
| G01N 3/04 | (2006.01) |
| B32B 7/12 | (2006.01) |
| C09J 7/02 | (2006.01) |

(52) U.S. Cl.
CPC ............... *G01N 19/04* (2013.01); *G01N 3/04* (2013.01); *C09J 7/0246* (2013.01)

(58) Field of Classification Search
CPC ............ B65D 85/36; G01N 19/04; G01N 2203/0017; G01N 2203/0091; G01N 2203/0266; G01N 2203/0282
USPC ................... 73/150 A, 826, 827; 174/110
See application file for complete search history.

(56) References Cited

U.S. PATENT DOCUMENTS

| 3,887,761 | A | * | 6/1975 | Gore | H01B 13/085 156/53 |
| 4,368,613 | A | * | 1/1983 | Sanchez | H01B 13/26 174/36 |
| 4,601,912 | A | * | 7/1986 | Arai | G11B 5/85 427/130 |
| 5,636,551 | A | * | 6/1997 | Davidson | D07B 1/162 29/434 |
| 6,478,264 | B1 | * | 11/2002 | Nelson | G01N 19/04 138/106 |
| 6,584,858 | B1 | * | 7/2003 | Miyazawa | G01N 19/04 73/150 A |
| 2011/0037687 | A1 | * | 2/2011 | Akamatsu | G01N 3/24 345/87 |
| 2011/0240332 | A1 | * | 10/2011 | Yamazaki | H01B 3/301 174/110 SR |
| 2012/0217035 | A1 | * | 8/2012 | Iwasaki | H01B 3/441 174/102 C |
| 2012/0238172 | A1 | * | 9/2012 | Siebert | B32B 5/022 442/334 |

FOREIGN PATENT DOCUMENTS

| GB | 2163262 A | 2/1986 |
| JP | 06-194304 A | 7/1994 |
| SU | 637649 A1 | 12/1978 |

OTHER PUBLICATIONS

Written Opinion and Search Report for Application No. 201304980-4 dated Aug. 5, 2014.

* cited by examiner

*Primary Examiner* — Gedeon M Kidanu
(74) *Attorney, Agent, or Firm* — Michael Stonebrook

(57) ABSTRACT

Representative implementations of devices and techniques provide a tape adhesion test system. The test system applies a pulling force to an outer layer of tape adhered to an inner layer of tape through an adhesive bond, while the inner layer of tape is secured to a portion of the test system. The pulling force is measured when the adhesive bond between the outer layer of tape and the inner layer of tape breaks.

18 Claims, 5 Drawing Sheets

TAPE ADHESION TEST SYSTEM

BACKGROUND

Electrical wire conductors may be insulated using various materials and techniques, depending on the desired application. Magnet wire refers to an insulated wire conductor suitable for making electromagnetic coils as used in electric motor windings, generators, and solenoids, for example. In subsurface applications, such as electric submersible pumps (ESP's) for the oil and gas industries, robust wire insulation may be created by wrapping the wire conductor being made into magnet wire within an insulating tape that is wound helically around the wire.

The National Electrical Manufactures Association (NEMA) publishes "Magnet Wire (MW) 1000," which describes ASTM and NEMA standards for magnet wire manufacturing and testing methods. MW 1000 is the standards publication for general requirements, product specifications, and test procedures for magnet wire. Currently there are no methods or standards that quantify the bond strength of the tape insulation on the wire.

BRIEF DESCRIPTION OF THE DRAWINGS

The detailed description is set forth with reference to the accompanying figures. In the figures, the left-most digit(s) of a reference number identifies the figure in which the reference number first appears. The same numbers are used throughout the figures to reference like features and components.

For this discussion, the devices and systems illustrated in the figures are shown as having a multiplicity of components. Various implementations of devices and/or systems, as described herein, may include fewer components and remain within the scope of the disclosure. Alternately, other implementations of devices and/or systems may include additional components, or various combinations of the described components, and remain within the scope of the disclosure.

DETAILED DESCRIPTION

Introduction

An example tape adhesion test system is described herein. The example system provides quantitative and qualitative information about the bond strength and thus the quality of the adhesive bond between layers of tape, as the layers are wound around tape-wrapped wire, such as magnet wire. The example system can also provide information about the bond strength and the quality of the adhesive bond between a layer of tape and the wire itself, or other article, wrapped by the tape. The tape adhesion of tape-wrapped magnet wire or other taped articles may be tested during manufacture or at other times in the life of a product.

The example tape adhesion test system can be used to improve the quality of magnet wire. Magnet wire is manufactured in several wire gauges (AWG) with layers of tape helically wrapped around a single metallic wire. The magnet wire is then wound in electric motors that power ESP systems and other products. In various embodiments, the metallic wire is comprised of copper, but may also be comprised of other conductive metals or alloys.

Various implementations and embodiments for tape adhesion test systems, devices, and techniques are discussed in this disclosure. Techniques and devices are discussed with reference to example tape adhesion test systems and devices illustrated in the figures. However, this is not intended to be limiting, and is for ease of discussion and illustrative convenience. The techniques, systems, and devices discussed may be applied to any of various tape adhesion test system designs, structures, and the like, and still remain within the scope of the disclosure. Further, the techniques, systems, and devices discussed with reference to magnet wire are applicable to and intended to include any tape-wrapped wire or tape-wrapped article. For convenience, the term "magnet wire" used herein also refers to any tape-wrapped wire or tape-wrapped article.

Embodiments are explained in more detail below using a plurality of examples. Although various embodiments and examples are discussed here and below, further embodiments and examples may be possible by combining the features and elements of individual embodiments and examples.

Figure 1:
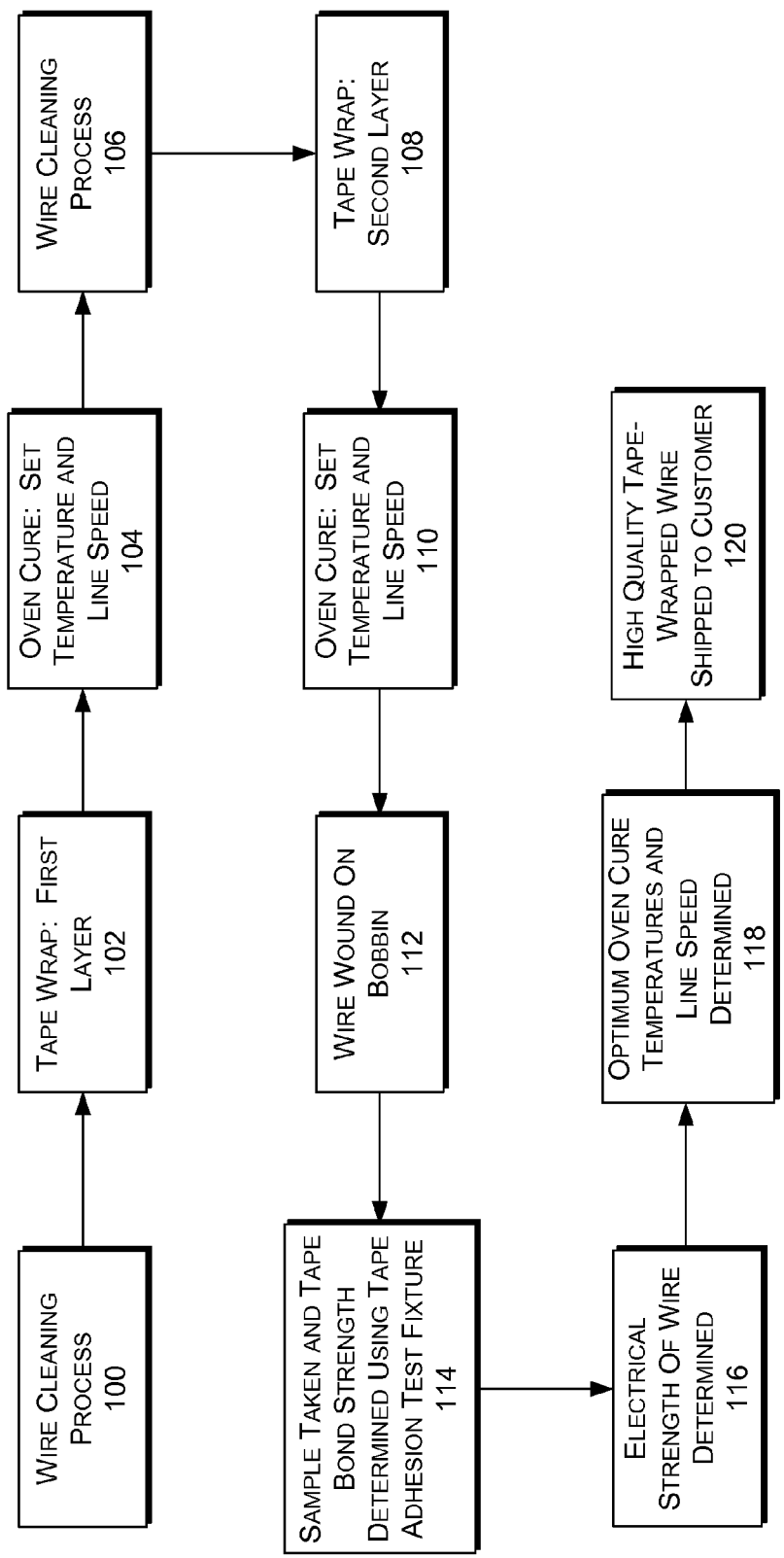
FIG. 1 illustrates an example manufacturing process for tape-wrapped wire, in accordance with one or more embodiments.

FIG. 1 shows an example manufacturing method for tape-wrapped wire, such as magnet wire. In the flow diagram, operations are shown as individual blocks. Example tape adhesion testing can be performed at multiple places in the example method to improve or optimize settings during manufacture. For example, tape adhesion testing can be performed to determine the settings to be used in blocks 104, 110, and 118. Testing is also performed at block 114 on a sample of the completed tape-wrapped wire, of a desired lot.

For instance, in an embodiment, an oven temperature and/or a line speed setting to be used for manufacturing (e.g., curing, for example) the tape-wrapped wire may be determined based on a pull force measured during the tape adhesion testing. One or more of the settings may be adjusted in response to the pull force measured, for example, if the pull force measured indicates a less-than-desirable tape adhesion bond. In the example, the tape adhesion testing can determine improved or optimum settings for achieving high quality magnet wire. High quality magnet wire, in turn can provide high quality and reliable ESPs.

A first bond, e.g., between a metallic conductor and the insulating tape, and a second bond e.g., between two layers of tape, can significantly impact the electrical properties and reliability of the magnet wire. Conventional test techniques and industry standards may test and consider the first bond, the tape-to-metal bond strength. The example tape adhesion test system can improve the testing and can quantify the strength of the second bond, the tape-to-tape bond, in addition to the tape-to-metal bond.

Knowing the strength of both the first and second bonds can enable the manufacture of high quality magnet wire, as discussed above. In an implementation, the tape adhesion test system can be made inexpensively and allows multiple sites to test magnet wire quality after shipment, and before the magnet wire is wound into a motor. The example tape adhesion test system can enable an industry standard for testing tape-to-tape adhesion.

As shown in FIG. 1, at block 100, metallic wire or other articles are cleaned in preparation for tape-wrapping. At block 102, a first layer of tape is wrapped onto the wire. In many embodiments, the tape is wrapped on the wire circumferentially and at an angle, forming a helix of tape around the wire. At block 104, the first layer of tape is oven cured on the wire. Settings for the oven temperature and the line speed for the curing process may be based on previous tape adhesion test measurements, incorporating possible adjustments for optimizing the bond strength. If desired, tape adhesion testing may be performed on a sample of the tape-wrapped wire at this stage (i.e., at block 104).

At block 106, the tape-wrapped wire is cleaned in preparation for further tape-wrapping. At block 108, a second layer of tape is wrapped around the wire in like manner to the first layer. At block 110, the second layer of tape is oven cured on the tape-wrapped wire. Settings for the oven temperature and the line speed for the curing process may be based on previous tape adhesion test measurements, incorporating possible adjustments for optimizing the bond strength. If desired, tape adhesion testing may be performed on a sample of the tape-wrapped wire at this stage (i.e., at block 110).

In various implementations, one or more additional layers of tape may be added to the tape-wrapped wire, as described above. At block 112, the completed tape-wrapped wire is wound onto a bobbin, for example. At block 114, a sample of the completed tape-wrapped wire is taken and adhesion tested. For example, the tape bond strength (i.e., between layers of tape and/or between the first layer of tape and the metallic wire) is determined using a tape adhesion test system as described further below. In various implementations, the tape adhesion test system may be used to perform tape adhesion testing at any other point in the manufacturing process, such as blocks 104, 110, and 118, for example.

At block 116, the electrical strength of the tape-wrapped wire is determined. For example, the insulating capability (i.e., dielectric strength, electric stress, etc.) of the tape-wrap insulation may be determined. The electrical strength or insulating capability may be based on the number of tape layers, the curing temperature used, the line speed of the oven, and so forth. Accordingly, settings for one or more of these parameters may be adjusted to optimize the electrical strength of the tape-wrap insulation on the wire.

At block 118, the electrical strength of the tape-wrapped wire and the tape adhesive bond strength(s) are correlated. In an implementation, a sample of the tape-wrapped wire may be tested for tape-to-tape and/or tape-to-wire bond strengths at this stage. In one implementation, the correlation includes determining an optimized oven curing temperature, line speed, or other setting of the manufacturing process, or combination of settings, that results in a tape-wrapped wire having an optimum desirable combination of electrical strength and adhesive bond strength.

At block 120, high quality tape-wrapped wire is shipped to the customer. In an implementation, high quality tape-wrapped wire is that tape-wrapped wire which has an optimized desirable combination of electrical strength and adhesive bond strength. The example tape adhesion test system described below can also be used by customers to determine the quality of tape-wrapped wire with respect to tape adhesiveness, after shipment.

Example Tape Adhesion Test System

Figure 2:
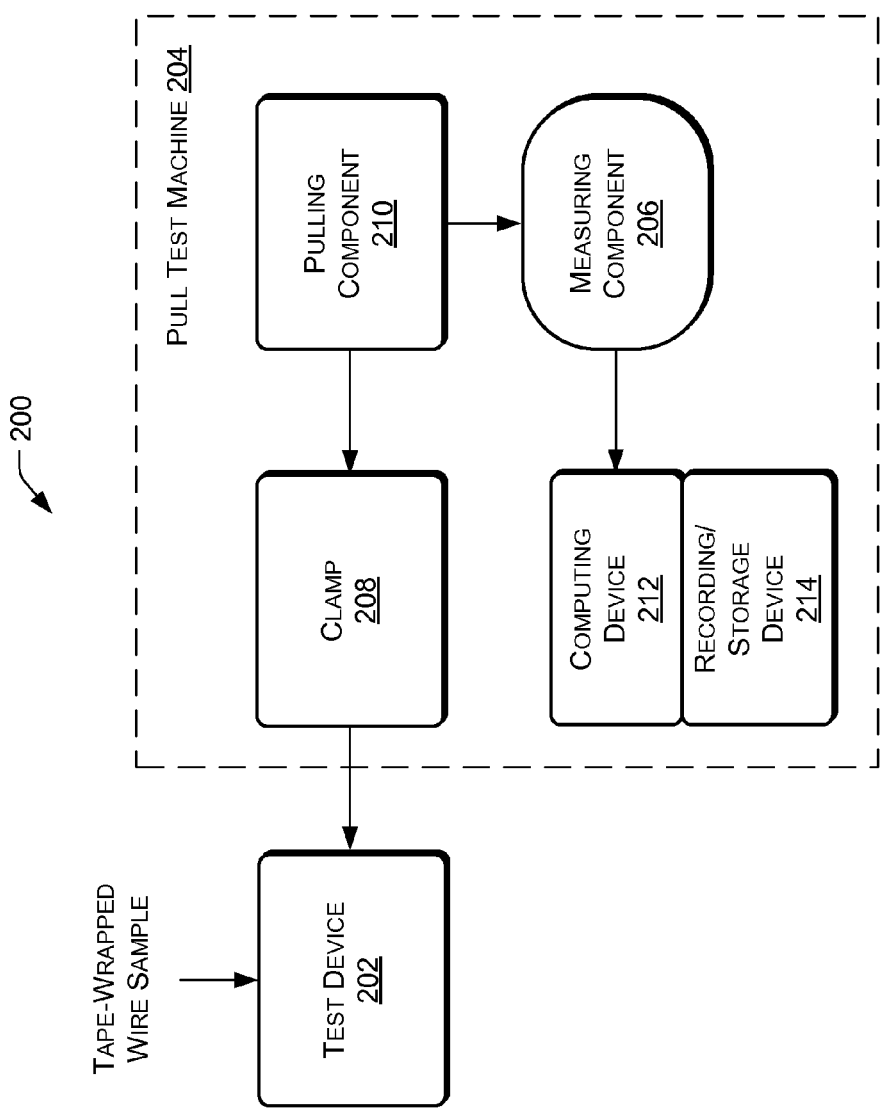
FIG. 2 illustrates example components in which embodiments of a tape adhesion test system can be implemented.

In FIG. 2, representative implementations of devices and techniques provide a tape adhesion test system ("test system") 200. In various implementations, the test system 200 is arranged to perform the tape adhesion testing on tape-wrapped wire described above. In an implementation, the test system 200 applies a pulling force to an outer layer of tape adhered to an inner layer of tape through an adhesive bond, while the inner layer of tape is secured to a portion of the test system 200. The pulling force is measured when the adhesive bond breaks, i.e., when the adhesive bond between the outer layer of tape and the inner layer of tape breaks.

In one embodiment, the test system 200 applies a pulling force to a layer of tape adhered to a metallic wire by an adhesive bond, while the metallic wire is secured to a portion of the test system 200. The pulling force is measured when the adhesive bond between the layer of tape and the metallic wire breaks.

FIG. 2 illustrates example components for implementing embodiments of a tape adhesion test system 200. In one embodiment, a test system 200 may include a test device 202 (described with reference to FIG. 3) and a pull test machine 204. In various implementations, the test device (e.g., test jig) 202 is arranged to secure a sample of tape-wrapped wire to the test system 200 for adhesion testing and the pull test machine (a.k.a., pull tester) 204 is arranged to apply a pulling force to a layer of tape on the sample during the testing. For example, in an embodiment, the test device 202 secures a first layer of tape to the test system 200 while the pull tester 204 applies a pulling force to a second layer of tape adhered to the first layer of tape through an adhesive bond. In an implementation, the pull tester 204 includes a measuring component 206, which measures the pulling force when the adhesive bond breaks, determining the tape-to-tape adhesive bond strength.

As shown in FIG. 2, an example pull tester 204 may include a clamp 208, a pulling component 210, and a computing device 212, as well as the measuring component 206. In an implementation, the computing device 212 may be coupled to a recording/storage device 214 arranged to record measurements of the measuring component 206, calculations of the computing device, settings of the manufacturing process, electrical properties of the tape-wrapped wire, and the like.

If included, the clamp 208 may be arranged to grip a layer of the tape of the sample tape-wrapped wire while the sample is secured to the test device 202. For example, the clamp 208 can grip a layer of tape for applying a pulling force to an outer layer of tape of the tape-wrapped wire during the adhesion testing. In various implementations, the clamp 208 may include various friction features on gripping surface(s) and may be constructed to firmly grip a tape layer during the testing.

In various embodiments, the pulling component 210 is coupled to the clamp 208 and provides the pulling force to the tape layer via the clamp 208. For example, the pulling component 210 may include a pneumatic, hydraulic, or electric cylinder or solenoid, a mechanical drive assembly, or another device or system arranged to provide a pulling force.

In various implementations, the pulling component 210 provides a pulling force to the tape layer that constantly or incrementally increases in magnitude. When the magnitude of the pulling force is great enough to break (i.e., overcome) the adhesive bond between the tape layer and an inner tape layer or the metallic wire, the pulling force is measured with the measuring component 206. In various embodiments, the measuring component 206 may comprise a mechanical or electronic force gauge, pull force meter, pull gauge, force tester, or the like.

In an implementation, the computing device 212 receives pulling force data (i.e., pulling force value(s)) from the measuring component 206. For example, the computing device 212 may receive the pulling force data when the adhesive bond breaks between an outer layer of tape and an inner layer of tape, separating the layers. The pulling force data may be recorded or stored using the recording/storage device 214, for instance.

In example embodiments, the computing device 212 (discussed further with reference to FIG. 4), in conjunction with the recording/storage device 214, relates the measured pulling force to properties of the tape-wrapped wire, such as the electrical properties discussed above. For example, in one embodiment, the computing device 212 including the recording/storage device 214 are arranged to relate or correlate the measured pulling force to properties and one or more manufacturing steps for magnet wire, as discussed above.

For instance, the measured adhesive bond strengths can be correlated with electrical tests (e.g., insulation strength tests, etc.) of the magnet wire to determine improved or optimal bond strength of the tape-to-tape bond and/or the tape-to-conductor bond, and to determine related manufacturing techniques (e.g., oven temperature, line speed, etc.) to achieve high quality magnet wire.

In an example, the computing device 212 can retrieve stored pulling force values and stored electrical test values from memory, or from the recording/storage device 214, and correlate the pulling force values and electrical test values to corresponding oven temperatures, line speeds, quantity of tape wraps, and other manufacturing steps. The computing device 212 can determine optimum combinations of oven temperatures, line speeds, quantity of tape wraps, and other manufacturing steps that result in characteristics desired for high quality magnet wire.

In various implementations, a tape adhesion test system 200 may include fewer, additional, or alternate components, and remain within the scope of the disclosure. One or more components of a tape adhesion test system 200 may be collocated, combined, or otherwise integrated with another component of the tape adhesion test system 200. Further, one or more components of the tape adhesion test system 200 may be remotely located from the other(s) of the components.

Example Test Device

Figure 3:
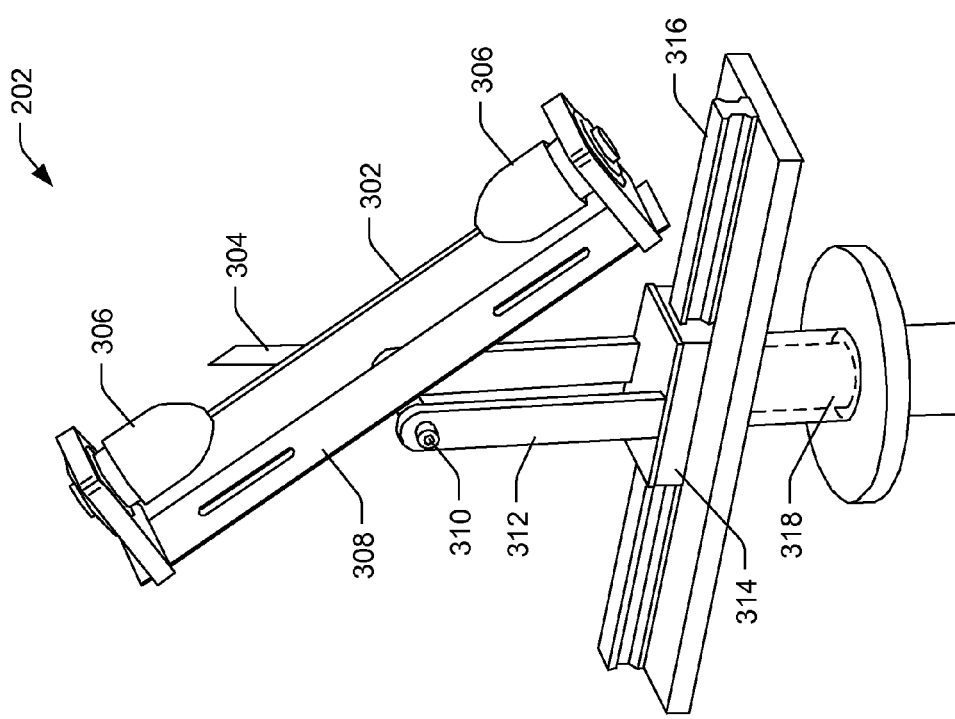
FIG. 3 illustrates example components in which embodiments of a test device of a tape adhesion test system can be implemented.

FIG. 3 illustrates example components in which embodiments of a test device 202 of a tape adhesion test system 200 can be implemented. In various implementations, the test device 202 is incorporated with the pull tester 204 to form the test system 200. For example, the test device 202 may be placed or secured to the pull tester 204 such that the clamp 208 can grip a tape layer 304 of the sample tape-wrapped wire 302. In some embodiments, the test device 202 is placed in or on the pull tester 204. In other embodiments, the test device 202 may be attached to the pull tester 204, placed in proximity to the pull tester 204, or the like. In one embodiment, the test device 202 and the pull tester 204 are integral components of a single machine. In another embodiment, the test device 202 is removable from the pull tester 204.

In an implementation, as shown in FIG. 3, the test device 202 includes one or more chucks 306 for securing each end of the tape-wrapped wire 302. For example, the chucks 306 may be tool or device-holding chucks arranged to grip the ends of the tape-wrapped wire 302, such that the tape-wrapped wire 302 is substantially taut. In other words, the tape-wrapped wire 302 has little or no slack, with or without stretching the tape-wrapped wire 302 between the chucks 306.

In various embodiments, the chucks 306 are coupled to a bracket 308. In an example embodiment, the chucks 306 are free to rotate with respect to the bracket 308. For example, when the tape-wrapped wire 302 is secured to the chucks 306, the tape-wrapped wire 302 (and the chucks 306) may rotate or spin with respect to the bracket 308. In an implementation, the tape-wrapped wire 302 will spin with respect to the bracket 308 when the tape layer 304 is pulled and the adhesive bond of the tape layer to an inner tape layer or to the metallic wire is broken.

In an implementation, as shown in FIG. 3, the bracket 308 includes a hinge 310. For example, in the implementation, the bracket 308 is hinged, and has freedom to tilt about a pivot (e.g., the hinge 310). In an implementation, the hinged bracket 308 is free to tilt about the pivot 310 when the pulling force is applied to the outer layer of tape 304 of the tape-wrapped wire 302.

In various embodiments, as shown in FIG. 3, the test device 202 includes one or more standards 312 coupled to and arranged to hold the hinged bracket 308 such that the bracket 308 is free to tilt about the pivot 310. The standard(s) 312 may have any configuration or design that allows the bracket 308 freedom to tilt.

In an implementation, as shown in FIG. 3, the test device 202 includes a slide 314 coupled to the hinged bracket 308. In various embodiments, the slide 314 includes a rail 316, or the like, arranged to allow the slide 314 to freely move in a substantially linear path within predefined bounds. For example, in an embodiment, the bracket 308 is coupled to the slide 314 (e.g., via the standard(s) 312) and is free to translate along the slide 314 (via the rail 316) when the pulling force is applied to the outer layer of tape 304 of the tape-wrapped wire 302.

In an implementation, as shown in FIG. 3, the test device 202 includes a hub 318 coupled to the hinged bracket 308. In various embodiments, the hub 318 is free to rotate in one or both directions, about an axis of the hub 318. For example, in an embodiment, the bracket 308 is coupled to the hub 318 (e.g., via the standard(s) 312) and is free to rotate about the axis of the hub 318 when the pulling force is applied to the outer layer of tape 304 of the tape-wrapped wire 302.

In various implementations, the test device 202 may include a combination of elements including one or more of the hinged bracket 308, the slide 314, and the hub 318. In one embodiment, as shown in FIG. 3, the test device 202 includes all three of the elements: the hinged bracket 308, the slide 314, and the hub 318. In the embodiment, the test device 202, as a unified component, can translate, rotate, and tilt when the pulling force is applied to the outer layer of tape 304 of the tape-wrapped wire 302. In various embodiments, this allows the test system 200 to be used with multiple gauges of wire and tape wrap designs.

In an implementation, as discussed above, the tape 304 may be wrapped circumferentially and at an angle around the tape-wrapped wire 302 forming a helix. A sample of the tape-wrapped wire 302 may be secured in the chucks 306 of the test device 202 for adhesion testing. A clamp 208 may be secured to an outer layer of the tape 304, for applying a pulling force to the outer layer of tape 304 of the tape-wrapped wire 302. As the pulling force is applied to the tape 304, the test device 202 may translate, rotate, and/or tilt, due to the helix configuration of the tape-wrap, as the tape is unwrapped from the tape-wrapped wire 302.

Example Computing Device

Figure 4:
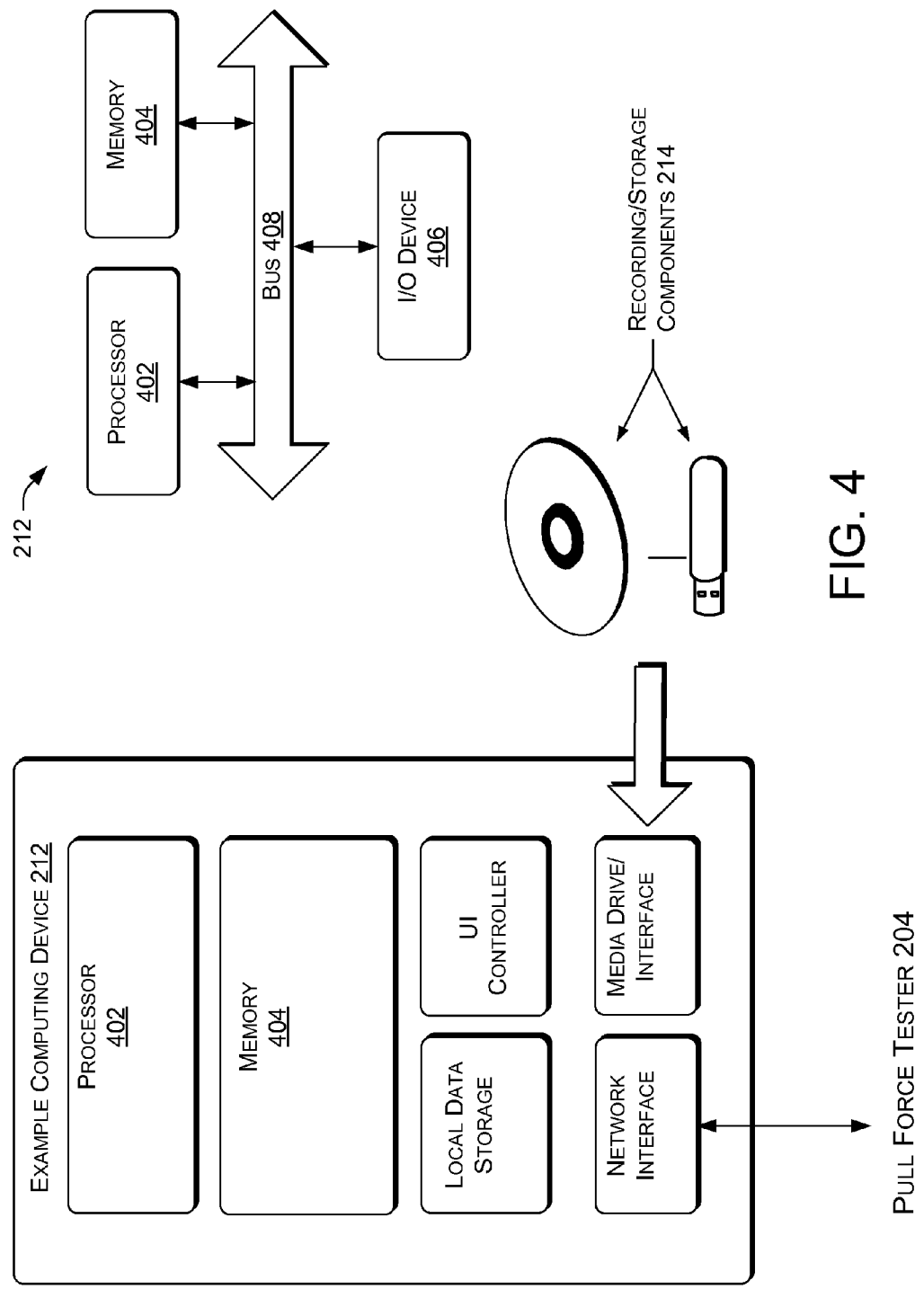
FIG. 4 illustrates various components of an example computing device that can be implemented in embodiments of a tape adhesion test system.

FIG. 4 illustrates various components of an example computing device 212 that can be implemented in embodiments of a tape adhesion test system 200. In various embodiments, the computing device 212 is arranged to receive measured properties of a magnet wire, and to relate the properties of the magnet wire to a design and manufacture of magnet wire. The computing device 212 can be implemented in association with an example tape adhesion text system 200 (a.k.a test fixture). For example, the computing device 212 can assist measurement of pull force and adhesion strength between tape layers. The computing device 212 can also relate measurements to properties of tape-wrapped wire 302 and improve or optimize design and manufacture of tape-wrapped wire 302 based on the measurements, as discussed above.

The example computing device 212 is only one example of a computing device and is not intended to suggest any limitation as to scope of use or functionality of the computing device 212 and/or its possible architectures. Neither should computing device 212 be interpreted as having any dependency or requirement relating to any one or combination of components illustrated in the example computing device 212.

Computing device 212 includes one or more processors or processing units 402, one or more memory and/or storage components 404, one or more input/output (I/O) devices 406, and a bus 408 that allows the various components and devices to communicate with one another. Bus 408 represents one or more of any of several types of bus structures, including a memory bus or memory controller, a peripheral bus, an accelerated graphics port, and a processor or local bus using any of a variety of bus architectures. Bus 408 can include wired and/or wireless buses.

Memory/storage component 404 represents one or more computer storage media. Component 404 can include volatile media (such as random access memory (RAM)) and/or non-volatile media (such as read only memory (ROM), Flash memory, optical disks, magnetic disks, and so forth). Component 404 can include fixed media (e.g., RAM, ROM, a fixed hard drive, etc.) as well as removable media (e.g., a Flash memory drive, a removable hard drive, an optical disk, and so forth).

One or more input/output devices 406 allow a user to enter commands and information to computing device 212, and also allow information to be presented to the user and/or other components or devices. Examples of input devices include a keyboard, a cursor control device (e.g., a mouse), a microphone, a scanner, and so forth. Examples of output devices include a display device (e.g., a monitor or projector), speakers, a printer, a network card, and so forth.

Various techniques may be described herein in the general context of software or program modules. Generally, software includes routines, programs, objects, components, data structures, and so forth that perform particular tasks or implement particular abstract data types. An implementation of these modules and techniques may be stored on or transmitted across some form of computer readable media. Computer readable media can be any available medium or media that can be accessed by a computing device. By way of example, and not limitation, computer readable media may comprise "computer storage media".

"Computer storage media" include volatile and non-volatile, removable and non-removable media implemented in any method or technology for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

In various implementations, the computing device 212 may be fully integrated with the test system 200, or may have some components separate or remote from components of the test system 200. For example, some processing for the computing device 212 may be located remotely (e.g., cloud, network, etc.). In another example, some outputs from the computing device 212 may be transmitted, displayed, or presented on a remote device or at a remote location.

The techniques, components, and devices described herein with respect to a tape adhesion test system 200 or a test device 202 are not limited to the illustrations in FIGS. 1-4, and may be applied to other systems, designs, and/or applications without departing from the scope of the disclosure. In some cases, additional or alternative components may be used to implement the techniques described herein. It is to be understood that a tape adhesion test system 200 may be stand-alone, or may be part of another system (e.g., integrated with other components, systems, etc.).

Representative Process

Figure 5:
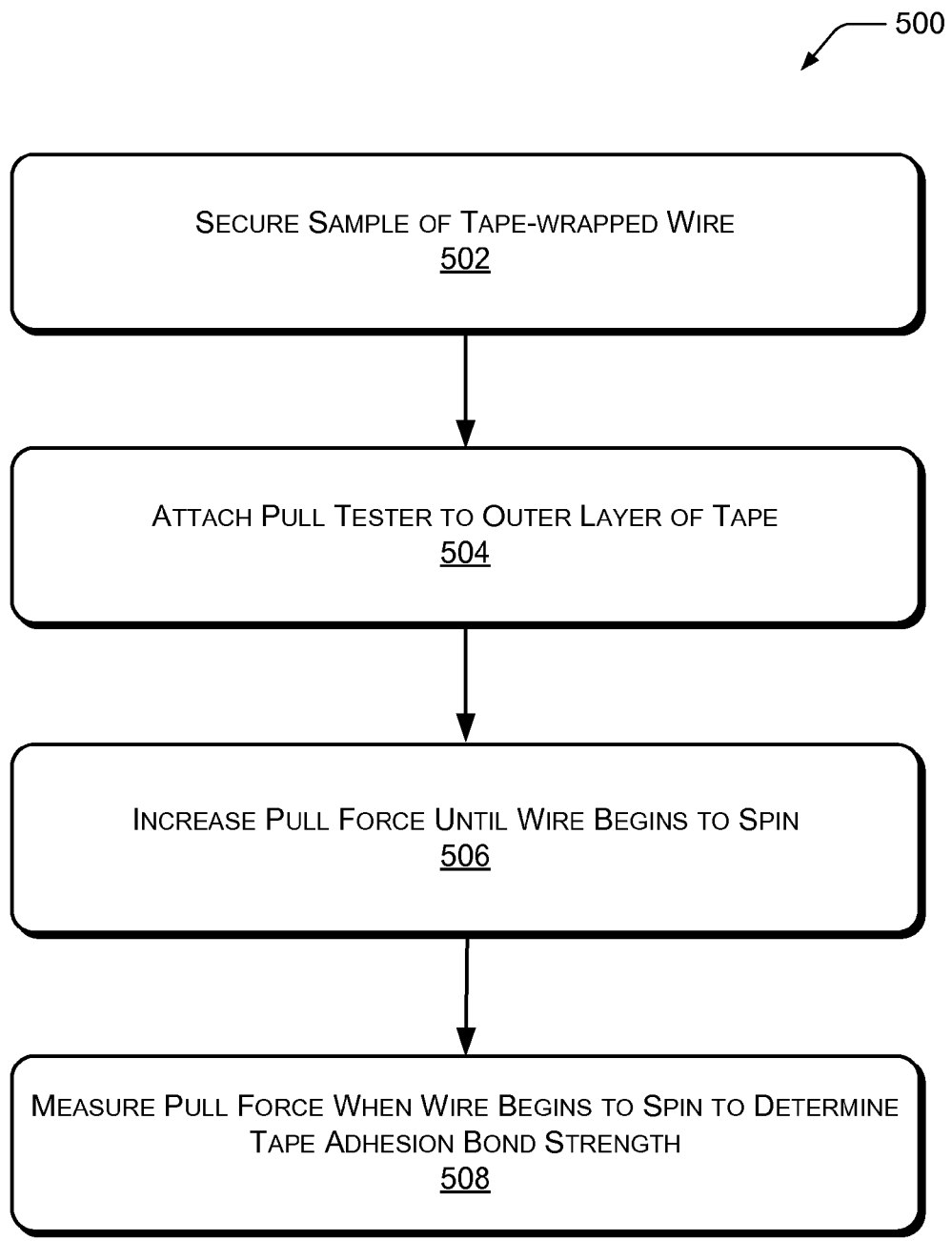
FIG. 5 illustrates an example method for tape adhesion testing, in accordance with one or more embodiments.

FIG. 5 illustrates a representative process 500 for testing a tape adhesiveness of a tape-wrapped wire, like magnet wire (such as tape-wrapped wire 302, for example). The process 500 is described with reference to FIGS. 1-4.

The order in which the process is described is not intended to be construed as a limitation, and any number of the described process blocks can be combined in any order to implement the process, or alternate processes. Additionally, individual blocks may be deleted from the process without departing from the spirit and scope of the subject matter described herein. Furthermore, the process can be implemented in any suitable materials, or combinations thereof, without departing from the scope of the subject matter described herein.

In an example embodiment, the process includes cutting a sample (an approximately six inch sample, for instance) of tape-wrapped wire from a bobbin of the tape-wrapped wire and removing a portion (approximately three inches, for example) of the outer layer of tape.

At block 502, the process includes placing the sample of tape-wrapped wire into one or more rotatable chucks (such as chuck 306, for example). In an embodiment, the process includes tightening the chucks onto each end of the sample. In various implementations, the chucks are components of a test device (such as test device 202, for example) that has several degrees of freedom of movement. In one implementation, the test device can translate, rotate, and/or tilt when a pulling force is applied to a tape layer of the sample tape-wrapped wire.

At block 504, the process includes attaching a pull tester (such as pull tester 204, for example) to an outer layer of tape adhered to an inner layer of tape of the tape-wrapped wire. For example, a clamp (such as clamp 208, for example) may be used to attach the pull tester to the outer tape layer. The clamp may be tightened to the outer tape layer for a secure grip during testing.

At block 506, the process includes increasing a pull force of the pull tester (via a pulling component such as pulling component 210, for example) until the wire begins to spin, indicating that the bond between the outer layer of tape and an inner layer of tape has been broken. In an alternate implementation, the outer layer of tape is adhered to the metallic wire of the tape-wrapped wire. In the implementation, the wire spins when the bond between the outer layer of tape and the metallic wire has been broken.

At block 508, the process includes measuring the pull force when the wire begins to spin to determine an adhesive bond strength. For example, the adhesive bond strength may be the bond between the outer layer of tape and the inner layer of tape or between the outer layer of tape and the metallic wire.

In various implementations, the pull force is measured using a measuring component (such as measuring component 206, for example) and is recorded or stored using a computing device (such as computing device 212) and/or a recording or storage device (such as recording/storage device 214).

In an embodiment, the process includes quantifying the adhesive bond strength between the outer layer of tape and the inner layer of tape and quantifying the adhesive bond strength between the inner layer of tape and a metallic wire conductor of the tape-wrapped wire. The quantified values may be stored for retrieval by the computing device, for example.

In various embodiments, the process includes improving a design of the tape-wrapped wire based on the measured pull force. For example, the process includes comparing the measured pull force to the physical and/or electrical properties of each wire sample and determining improved or optimal manufacturing methods based on the comparison, as described above.

For example, the process may also include improving one or more manufacturing processes of the tape-wrapped wire based on the measured pull force. In one example, the process includes correlating the measured pull force to one or more electrical properties (e.g., insulation strength, etc.) of the sample of the tape-wrapped wire to improve the manufacturing process. In the example, the process includes determining an oven temperature and a line speed setting for manufacture of the tape-wrapped wire based on the measured pull force, as described above.

In alternate implementations, other techniques may be included in the process 500 in various combinations, and remain within the scope of the disclosure.

CONCLUSION

Although only a few example embodiments have been described in detail above, those skilled in the art will readily appreciate that many modifications are possible in the example embodiments without materially departing from a tape adhesion test system. Accordingly, all such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. §112(f) for any limitations of any of the claims herein, except for those in which the claim expressly uses the words 'means for' together with an associated function.

What is claimed is:

1. A tape adhesion test system, comprising:
    means for securing a wire conductor that comprises a first layer of tape and a second layer of tape;
    means for sliding the wire conductor;
    means for applying a pulling force to a portion of the second layer of tape that is adhered to a portion of the first layer of tape through an adhesive bond wherein the means for sliding provides for translating the wire conductor responsive to an applied pulling force that breaks the adhesive bond; and
    means for measuring the pulling force when the adhesive bond breaks.

2. The tape adhesion test system of claim 1, wherein the first layer of tape is adhered to a wire conductor.

3. The tape adhesion test system of claim 2, further comprising means for measuring an adhesion of the first layer of tape to the wire conductor.

4. The tape adhesion test system of claim 2, wherein the wire conductor comprises a magnet wire.

5. The tape adhesion test system of claim 2, further comprising means for correlating the measured pulling force to electrical properties of a magnet wire.

6. The tape adhesion test system of claim 2, further comprising means for correlating the measured pulling force to bond strength achieved by a manufacturing step for a magnet wire.

7. The tape adhesion test system of claim 6, further comprising a computing device for measuring the pulling force and relating the pulling force to properties and manufacturing steps of a magnet wire.

8. A test fixture, comprising:
    chucks for securing each end of a tape-wrapped wire;
    a clamp for applying a pulling force to an outer layer of tape of the tape-wrapped wire;
    a recorder for storing a pulling force value when an adhesive bond between the outer layer of tape and an inner layer of tape separates;
    a hinged bracket to hold the chucks, the hinged bracket having freedom to tilt about a pivot when the pulling force is applied to the outer layer of tape of the tape-wrapped wire; and
    a slide coupled to the hinged bracket, the hinged bracket having freedom to translate along the slide when the pulling force is applied to the outer layer of tape of the tape-wrapped wire.

9. The test fixture of claim 8, further comprising a hub coupled to the hinged bracket, the hinged bracket having freedom to rotate about an axis of the hub when the pulling force is applied to the outer layer of tape of the tape-wrapped wire.

10. A method, comprising:
    placing a sample of a tape-wrapped wire into a rotatable and translatable chuck;
    attaching a pull tester to an outer layer of tape adhered to an inner layer of tape of the tape-wrapped wire;
    increasing a pull force of the pull tester until the chuck begins to rotate and translate;
    measuring the pull force when the chuck begins to rotate and translate to determine an adhesive bond strength between the outer layer of tape and the inner layer of tape.

11. The method of claim 10, further comprising quantifying the adhesive bond strength between the outer layer of tape and the inner layer of tape and quantifying the adhesive bond strength between the inner layer of tape and a metallic wire conductor of the tape-wrapped wire.

12. The method of claim 10, further comprising improving a design of the tape-wrapped wire based on the measured pull force.

13. The method of claim 10, further comprising improving a manufacturing process of the tape-wrapped wire based on the measured pull force.

14. The method of claim 13, further comprising correlating the measured pull force to one or more electrical properties of the sample of the tape-wrapped wire to improve the manufacturing process.

15. The method of claim 13, further comprising determining an oven temperature and a line speed setting for manufacture of the tape-wrapped wire based on the measured pull force.

16. The method of claim 13, further comprising selecting a tape adhesive based on the measured pull force.

17. The method of claim 13, further comprising changing a wrapping angle of tape being applied to the tape-wrapped wire based on the measured pull force.

18. The method of claim 13, further comprising changing a helix spacing of the tape-wrapped wire based on the measured pull force.

* * * * *